(12) United States Patent
Brust et al.

(10) Patent No.: US 6,335,158 B2
(45) Date of Patent: *Jan. 1, 2002

(54) METHODOLOGIES FOR THE DETECTION OF HUMAN IMMUNODEFICIENCY VIRUS NUCLEIC ACIDS EMPLOYING OLIGONUCLEOTIDE PRIMER DERIVED FROM THE HIV-1 MVP5180/91 GENOME

(75) Inventors: Stefan Brust, Marburg-Michelbach; Stefan Knapp; Manfred Gerken, both of Marburg; Lutz G. Guertler, Munich, all of (DE)

(73) Assignee: Dade Behring Marburg GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/131,551

(22) Filed: Aug. 10, 1998

Related U.S. Application Data (62) Division of application No. 08/394,021, filed on Feb. 23, 1995, now Pat. No. 5,830,634.

(30) Foreign Application Priority Data

Feb. 23, 1994 (DE) .......................................... 44 05 810

(51) Int. Cl.[7] .............................. C12Q 1/70; C12Q 1/68
(52) U.S. Cl. ........................... 435/5; 435/6; 424/188.1; 536/23.72; 536/24.3
(58) Field of Search ............................... 435/5, 6, 91.1, 435/91.2; 536/23.72, 24.3, 24.13

(56) References Cited

U.S. PATENT DOCUMENTS

| | | | |
|---|---|---|---|
| 4,629,783 A | 12/1986 | Cosand | 530/324 |
| 4,683,195 A | 7/1987 | Mullis et al. | 435/6 |
| 4,683,202 A | 7/1987 | Mullis | 435/91 |

FOREIGN PATENT DOCUMENTS

| | | |
|---|---|---|
| DE | 43 18 186 | 1/1995 |
| EP | 0345 375 A1 | 9/1988 |
| EP | 0 239 425 | 11/1989 |
| EP | 0591 914 A2 | 5/1993 |
| WO | WO 86/02383 | 4/1986 |
| WO | WO 89/12094 | 12/1989 |

OTHER PUBLICATIONS

L. Ratner et al., "Complete Nucleotide Sequence of the AIDS Virus, HTLV–III", Nature, vol. 313, Jan. 1985, pp. 277–284.

F. Laure et al., "Detection of HIV1 DNA in Infants and Children by Means of the Polymerase Chain Reaction", The LANCET, Sep. 3, 1988, pp. 538–541.

H. Tanimori et al., "A Sandwich Enzyme Immunoassay of Rabbit Immunoglobulin G with an Enzyme Labeling Method and a New Solid Support", Journal of Immunological Methods, 62 (1983), pp. 123–131.

F. Barre–Sinoussi et al., "Isolation of a T–Lymphotropic Retrovirus from a Patient at Risk for Acquired Immune Deficiency Syndrome (AIDS)", Science, vol. 220, May 1983, pp. 868–871.

S. Benn et al., "Genomic Heterogeneity of AIDS Retroviral Isolates from North America and Zaire", Science, vol. 230, Nov. 1985, pp. 949–951.

G. Barani et al., "The Peptides, Analysis, Synthesis and Biology", vol. 2, Acad. Press 1980, Chapter 1, pp. 3–284.

E.M. Southern, "Detection of Specific Sequences Among DNA Fragments Separated by Gel Electrophoresis", J. Mol. Biol., vol. 98, (1975), pp. 503–517.

F. Clavel et al., "Isolation of a New Human Retrovirus from West African Patients with AIDS", Science, Vol. Jul. 1986, pp. 343–346.

G. Myers et al., "Human Retroviruses and AIDS 1993 III–V", A Compilation and Analysis of Nucleic Acid and Acid Sequences, (1993).

G. Myers et al., "Human Retroviruses and AIDS 1992", A Compilation and Analysis of Nucleic Acid and Amino Sequences, (1992).

R.W. Coombs et al., "Plasma Viremia as an Endpoint in Evaluating the Effectiveness of Drugs Against Human Immunodeficiency Virus Type–1 (HIV) Infection: Natural History of Plasma Viremia and Monitoring of Antiretroviral Therapy", Viral Quantitation in HIV Infection, 1991, pp. 9–19.

(List continued on next page.)

Primary Examiner—Laurie Scheiner
Assistant Examiner—Jeffrey S. Parkin
(74) Attorney, Agent, or Firm—Heller Ehrman White & McAuliffe LLP (57) ABSTRACT

The present invention is directed toward nucleic-acid based methodologies for the detection of human immunodeficiency virus (HIV) nucleic acids in a sample. A novel HIV-1 isolate, designated MVP5180/91, was isolated from a West African Cameroonian patient with immunodeficiency. Nucleic acid and amino acid sequence comparisons of this isolate, with other HIV-1 strains of subtypes A–E and HIV-2 isolates, demonstrated that this virus shares only limited homology with other known HIV-1 and -2 isolates. However, this virus does display some genetic relatedness to another Cameroonian isolate designated ANT-70. These viruses form the basis for a new HIV-1 group which has been designated subtype O. An immunologically important epitope, corresponding to amino acids 601–623 of the MVP5180/91 transmembrane envelope glycoprotein, was identified. Labeled nucleic acids can be prepared from the nucleotide sequence encoding this region and employed in standard hybridization assays to detect HIV-1 nucleic acids. Alternatively, oligonucleotide primers can also be prepared from this region and employed in polymerase chain reaction (PCR) assays to detect viral-specific nucleic acids.

2 Claims, 3 Drawing Sheets

OTHER PUBLICATIONS

C. Ou et al., "DNA Amplification for Direct Detection of HIV–1 in DNA of Peripheral Blood Mononuclear Cells", Science, vol. 239, Jan. 1988, pp. 295–297.

S. Knapp et al., "pSEM Vectors: High Level Expression of Antigenic Determinants and Protein Domains", BioTechniques, vol. 8, No. 3, 1990, pp. 280–281.

T. Maniatis et al., "Molecular Cloning, A Laboratory Manual", 2nd Ed. Cold Spring Harbour Laboratory Press pp. 404–433.

C. Stahli et al, "High Frequencies of Antigen–Specific Hybridomas: Dependence on Immunization Parameters Prediction by Spleen Cell Analysis", J. of Immunol. Meth. 32, 1980, pp. 297–304.

G. Kohler et al., "Continuous Cultures of Fused Cells Secreting Antibody of Predefined Specificity", Nature, vol. 256, Aug. 1975, pp. 495–497.

King et al., "Preparation of Protein Conjugates via Intermolecular Disulfide Bond Formation", Biochemistry, vol. 17, No. 8, 1978, pp. 1499–1506.

Gurtler et al., Further Characterization of a new HIV–1 . . . Int. Conf. AIDS (Germany), 9(1): Abstract No. PO–A10–0147 (6/93).

Rehle et al., Preliminary characterization of a HIV–1 Variant, Int. Conf. AIDS (Netherlands), 8(3): Abstract No. PuA 6138, 7/92.

Agut et al., The Lancet, "Isolation of a typical HIV–1–Related Retrovirus from AIDS Patient", 340:681–82 (1992).

METHODOLOGIES FOR THE DETECTION OF HUMAN IMMUNODEFICIENCY VIRUS NUCLEIC ACIDS EMPLOYING OLIGONUCLEOTIDE PRIMER DERIVED FROM THE HIV-1 MVP5180/91 GENOME

This application is a divisional of application Ser. No. 08/394,021, filed Feb. 23, 1995 now U.S. Pat. No. 5,830,634.

BACKGROUND OF THE INVENTION

The present invention relates immunologically active peptides derived from a novel retrovirus of the HIV group, MVP5180/91. The invention further relates to the use of these peptides in diagnostic compositions and as immunogens.

Retroviruses which belong to the HIV group give rise to, in humans infected with them, to disease symptoms which are summarized under the collective term immune deficiency or AIDS (acquired immune deficiency syndrome). Epidemiological studies demonstrate that the human immunodeficiency virus (HIV) represents the etiological agent for the overwhelming majority of AIDS cases. A retrovirus which was isolated from a patient and characterized in 1983 was given the designation HIV-1 (Barré-Sinoussi, F. et al., *Science* 220: 868–871 (1983)). A variant of HIV-1 is described in WO 86/02383.

Until 1993, the known HIV-1 isolates were categorized into the five subtypes A–E on the basis of sequence comparisons and epidemiological standpoints (G. Myers et al., *Human Retroviruses and AIDS* 1992. "A compilation and analysis of nucleic acid and amino acid sequences." Los Alamos Laboratory, Los Alamos, USA (1992)).

A second group of human immunodeficiency viruses was identified in West Africa in 1985 (Clavel, F. et al., *Science* 233: 343–346 (1986) and designated human immunodeficiency virus type 2 (HIV-2) (EP-A-0 239 425). While HIV-2 retroviruses clearly differ from HIV-1, they also are related to monkey SIV immunodeficiency viruses. Like HIV-1, HIV-2 also gives rise to AIDS symptoms.

EP-A-0 345 375 describes another variant of an immunodeficiency retrovirus, which is designated HIV-3 retrovirus (ANT 70). The isolation of a different variant of immunodeficiency virus is also described in Lancet 340: 681–682 (1992).

Human immunodeficiency viruses characteristically exhibit a high degree of variability which significantly complicates attempts to compare the different isolates. For example, when comparing diverse HIV-1 isolates, high degrees of variability occur in some regions of the genome while other genome regions are comparatively well conserved (Benn, S. et al. *Science* 230: 949–951 (1985)). A substantially greater degree of polymorphism also has been observed in HIV-2 (Clavel, F. et al., *Nature* 324: 691–695 (1986)). The highest degree of genetic stability is possessed by regions in the gag and pol genes, which encode proteins which are structurally and enzymatically essential; some regions in the env gene, and also the genes (vif, vpr, tat, rev and nef) which encode regulatory proteins, exhibit a high degree of variability. In addition, it has also been demonstrated that antisera against HIV-1 also cross-react with gag and pol gene products from HIV-2 although only a low degree of sequence homology was present. These two viruses also did not hybridize with each other to any significant extent unless conditions of very low stringency were used (Clavel, F. et al., *Nature* 324: 691–695 (1986)).

In view of the wide dissemination of the retroviruses of the HIV group, and to the fact that there is a period lasting from a few to many years (2–20) between the time of infection and the time at which unambiguous symptoms of pathological changes are recognizable, it is of great importance epidemiologically that infection with retroviruses of the HIV group be detected as early as possible and, in particular, in a reliable manner. This is not only of importance when diagnosing patients who exhibit signs of immune deficiency, but also for screening blood donors. However, antibodies cannot be detected, or can be detected only weakly, in some sera when retroviruses of the HIV-1 or HIV-2 type, or constituents of these viruses, are used in detection systems. This is true even though the patients from which the sera are derived exhibit signs of immune deficiency. Thus, a need exists for a better method for detecting HIV infection, which does not use the previously known HIV-1 or HIV-2 type antigens.

Recently, another retrovirus that causes immune deficiency has been discovered. MVP5180/91 was isolated in 1991 from the peripheral lymphocytes of a 34-year old female patient from the Cameroons who exhibited signs of immune deficiency. This retrovirus originates geographically from a region in Africa which is located between West Africa, where infection with HIV-1 and HIV-2 viruses is endemic, and East Africa, where it is almost exclusively HIV-1 which is present. DE 43 18 186 describes nucleotide sequences from the viral genome of MVP5180/91 and amino acid sequences deduced therefrom. This retrovirus has been deposited, in accordance with the terms of the Budapest Treaty, in the European Collection of Animal Cell Cultures (ECACC) under the number V 920 92 318.

Similar to HIV-1 and HIV-2, MVP5180/91 grows in the following cell lines: HUT 78, Jurkat cells, C8166 cells and MT-2 cells. The isolation and multiplication of viruses are described in detail in *Viral Quantitation in HIV Infection*, Jean-Marie Andrieu (Ed.), John Libbey Eurotext (1991). The procedures described in that publication are incorporated herein by reference.

MVP5180/91 possesses a magnesium-dependent reverse transcriptase, which is not manganese-dependent. This represents a further feature possessed in common with the HIV-1 and HIV-2 viruses.

While anti-env antibodies in sera from German patients who are exhibiting signs of immune deficiency are weakly detected using the virus MVP5180/91, the sera react strongly when an HIV-1 virus is used instead of MVP5180/91 (DE 43 18 186). This stronger detection reaction was located principally in the gp41 protein. Thus, MVP5180/91 and HIV-1 are immunologically distinct.

The reliable detection of HIV infection is of particular interest today in connection with blood donation. In relation to ensuring the viral safety of blood and blood products, the immunochemical testing of individual donations in blood banks for HIV-1 antibodies became obligatory once specific anti-HIV-1 tests became available in 1985. After HIV-2 had been discovered in 1986, it became clear that it was not possible to detect HIV-2-specific antibodies as reliably with established HIV-1 tests as it was to detect anti-HIV-1 using corresponding HIV-1 antibody tests. Since 1989, "combination tests" have been available which permit the simultaneous, non-differentiating, detection of anti-HIV-1 and anti-HIV-2. The majority of commercially available anti-HIV-1/anti-HIV-2 combination tests are based on HIV antigens which have been prepared recombinantly or by peptide synthesis.

Whereas the use of HIV-1 and HIV-2 antigens in the diagnosis of retrovirus infection is well-known, the diagnostic significance of the peptides from MVP5180/91 have thus far not been determined.

SUMMARY OF THE INVENTION

It is therefore an object of the present invention to provide an immunologically active peptide comprising at least 15 consecutive amino acids selected from the amino acids in the following sequence (SEQ ID NO:1):
VWGIRQLRARLQALETLIQNQQRLNLWGXKGKLIXYTSVKWNTSWSGR,
wherein X is C or S. This peptide detects antibodies against retroviruses of the HIV type.

The invention further relates to a kit for detecting antibodies against viruses which cause immune deficiency comprising the above described peptide.

The invention further relates to a diagnostic agent for detecting an antibody against a retrovirus that causes immune deficiency, the diagnostic agent comprising the above described peptide and a detectable label that is capable of detecting the binding of the peptide with the antibody.

In another embodiment, the invention relates to a method of detecting the presence of anti-retrovirus antibodies in a sample, the method comprising contacting the sample with the above described diagnostic agent and detecting the presence of antibody bound to the diagnostic agent as a result of the contacting.

Another embodiment of the invention relates to an immunogen comprising (a) an amount of the above described peptide and (b) a physiologically-acceptable excipient therefor, wherein said amount is sufficient to elicit an immune response that is protective of a susceptible mammal against retrovirus infection.

In another embodiment, the invention relates to a method of immunizing a mammal against retrovirus infection, comprising administering to the mammal an effective amount of the above described immunogen.

Another embodiment of the present invention relates to an isolated DNA molecule which encodes the above described peptide.

Another embodiment relates to a method of detecting in a sample nucleic acids encoding a retrovirus that causes immune deficiency, comprising the steps of: (a) hybridizing a labeled DNA molecule to nucleic acids encoding a retrovirus in said sample, wherein said labeled DNA molecule is prepared by labeling the above described DNA molecule with a detectable label, and (b) detecting the hybridizing by means of said detectable label.

In another embodiment, the invention relates to a method of detecting in a sample nucleic acids encoding a retrovirus that causes immune deficiency, comprising subjecting said nucleic acids to a Polymer Chain Reaction (PCR), wherein the PCR employs at least two oligonucleotide primers that anneal to a nucleic acid encoding a retrovirus that causes immune deficiency, wherein one of the primers is complementary to a first nucleotide sequence comprising the sequence of the above described DNA molecule, or its complementary sequence, wherein the other primer is complementary to a second nucleotide sequence comprising a nucleic acid molecule encoding a retrovirus that causes immune deficiency, whereby a geometrically amplified product is obtained only when the first and second nucleotide sequences occur within the same nucleic acid molecule encoding a retrovirus that causes immune deficiency.

DETAILED DESCRIPTION OF THE PREFERRED EMBODIMENTS

Although German Patent Application No. DE 43 18 186 describes the isolation, cloning and sequencing of a novel immunodeficiency virus designated MVP5180/91, no peptides from this virus have been recognized yet as being immunologically active. The present invention is based on the discovery that certain peptides from MVP5180/91 are immunologically active and capable of detecting antibodies against a retrovirus that cause immune deficiency.

MVP5180/91 is different from HIV-1 and HIV-2. In order to achieve a better understanding of the differences between MVP5180/91 and the HIV-1 and HIV-2 retroviruses; the present inventors provide the following discussion of the structure of the retroviruses which cause immune deficiency. The RNA is located in the interior of the virus in a cone-shaped core which is assembled from protein subunits which carry the designation p24 (p for protein). This inner core is surrounded by a protein coat which is constructed from the protein pl7 (outer core). The virus is surrounded by a glycoprotein coat which, in addition to lipids and other constituents, contains the transmembrane protein gp41 and the outer membrane protein gp120. This gp120 binds to the CD4 receptors of the host cells.

Figure 1:
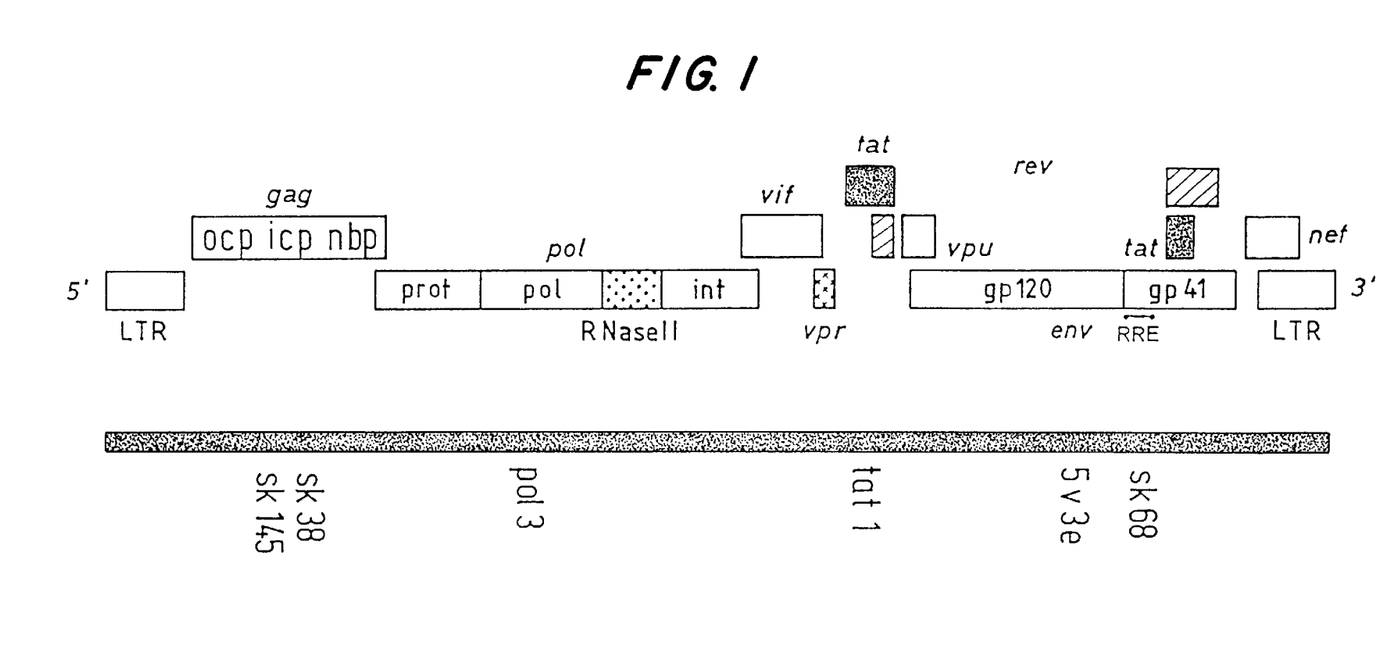
FIG. 1 is a diagram of the genome arrangement of the retrovirus HIV-1.

The RNA of the HIV viruses possesses the following gene regions: so-called long terminal repeats (LTR) at the two ends and the following gene regions gag, pol, env and nef. The gene gag encodes, inter alia, the core proteins, p24 and pl7, the gene pol encodes, inter alia, the reverse transcriptase, the RNAse H and the integrase, and the gene env encodes the glycoproteins gp41 and gp120 of the viral coat. The gene nef encodes a protein having a regulatory function. The genome arrangement of retroviruses of the HIV type is shown diagrammatically in FIG. 1.

Figure 2:
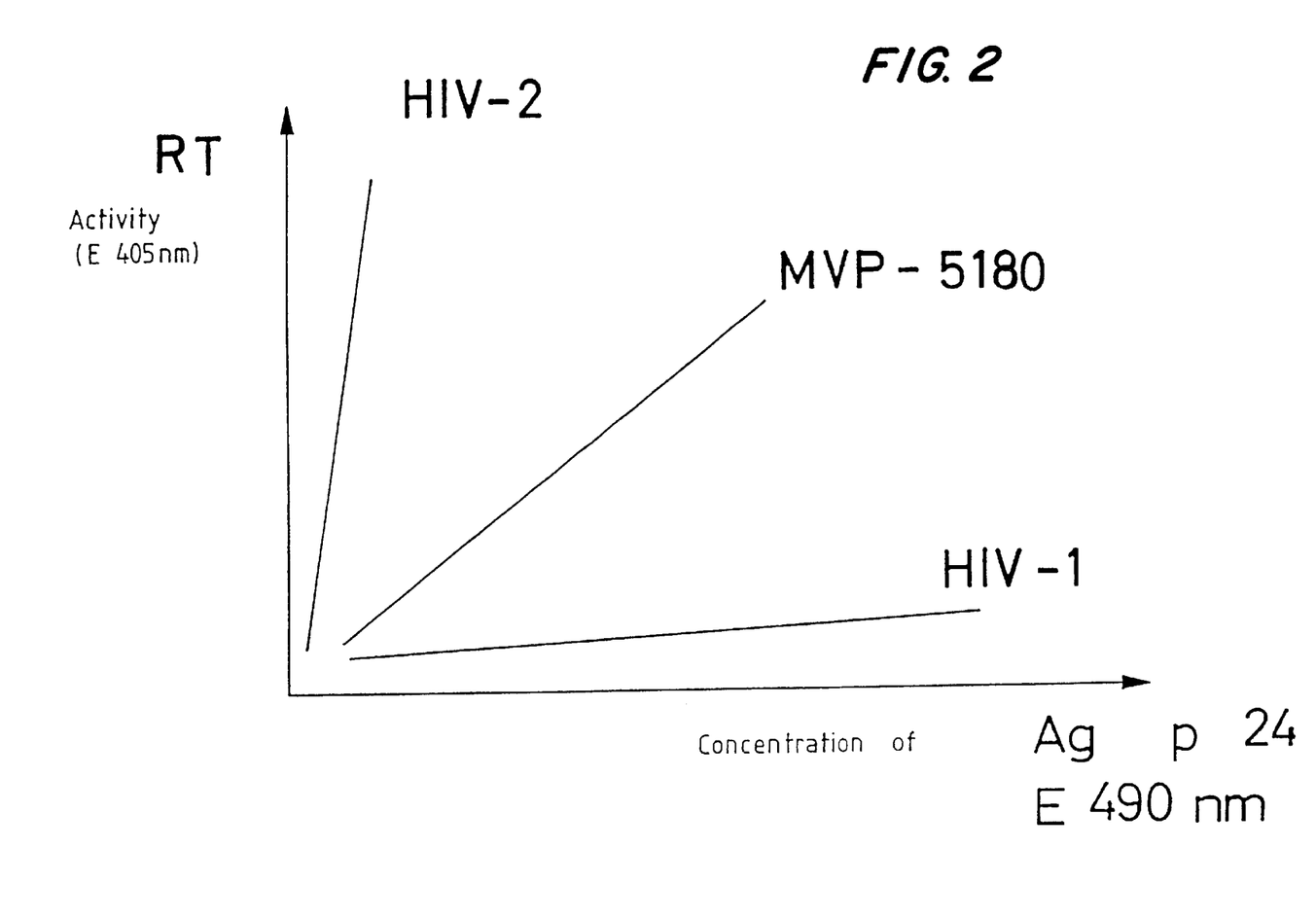
FIG. 2 is a graph showing the extinction at E 490 nm of HIV-1 and HIV-2 obtained by means of the antigen/antibody reaction plotted against the activity of reverse transcriptase.

The retroviruses HIV-1 and HIV-2 can be differentiated from each other by testing the viral antigen with a monoclonal antibody which is obtainable commercially as a test kit from Abbott (HIVAG-1 Monoclonal) and which is directed against the (HIV-1) p24. It is known that the content of reverse transcriptase is approximately the same in the HIV-1 and HIV-2 virus types. Therefore, if, in dilutions of the disrupted viruses, the extinction (E 490 nm) obtained by means of the antigen/antibody reaction, is plotted against the activity of the reverse transcriptase, a graph is then obtained which corresponds approximately to that in FIG. 2. This shows that, in the case of HIV-1 the monoclonal antibody employed has a very high binding affinity for p24 in relation to the content of reverse transcriptase. By contrast, the monoclonal antibody is found to have only a very low binding affinity for HIV-2 p24, again in relation to the content of reverse transcriptase in this virus. The present inventors discovered that when these measurements are carried out on MVP5180/91, the curve is found to be located almost exactly halfway between the curves for HIV-1 and HIV-2, i.e., the binding affinity of the monoclonal antibody towards MVP5180/91 p24 is reduced as compared with the situation in HIV-1. FIG. 2 shows this state of affairs diagrammatically, with RT denoting reverse transcriptase and the protein p24 being employed as antigen (Ag) against which the monoclonal antibody, which is present in the test kit obtainable commercially from Abbott, is directed.

MVP5180/91 has been further distinguished from HIV-1 and HIV-2 using Polymerase Chain Reaction ("PCR"). PCR is widely applied in gene technology, and the necessary components for carrying out PCR is commercially available. Briefly, PCR involves the amplification of DNA sequences when regions of the DNA sequence to be amplified are known. Short, complementary DNA fragments (oligonucleotide=primers), which anneal to a short region of the nucleic acid sequence to be amplified, are synthesized. In order to carry out the test, HIV nucleic acids are introduced together with the primers, into a reaction mixture which also contains a polymerase and nucleotide triphosphates. The polymerization (DNA synthesis) is carried out for a defined time and the nucleic acid strands are then separated by heating. After cooling, the polymerization then starts again. If the novel retrovirus is an HIV-1 or HIV-2 virus, it is possible to amplify the nucleic acid sequence by using primers which are conserved within the known sequences of the HIV-1 and HIV-2 viruses. Some primers of this nature have been described previously (Lauré, F. et al., *Lancet* ii: 538–541 (1988) for pol 3 and pol 4, and Ou, C. Y. et al., *Science* 239: 295–297 (1988) for sk 38/39 and sk 68/69). It has been discovered that when the above described process was applied, no amplification, or only weak amplification, of the MVP5180/91 DNA was obtained using previously described primer pairs (DE 43 18 186).

Western blot (immunoblot) analysis also has been helpful in distinguishing MVP5180 from HIV-1 and HIV-2. The western blot method is a common means for detecting HIV antibodies. In this method, the viral proteins are fractionated by gel electrophoresis and then transferred to a membrane. The membranes carrying the transferred proteins are then brought into contact with sera from the patients under investigation. Any antibodies against the viral proteins which are present will bind to these proteins. After washing, the only antibodies which remain are those which are specific for viral proteins. The antibodies are then visualized using anti-antibodies which, as a rule, are coupled to an enzyme which catalyzes a color reaction. In this way, the bands of the viral proteins can be rendered visible.

When the above western blot procedures were applied to MVP5180/91, MVP5180/91 exhibits two important and significant differences in comparison to the HIV-1 and HIV-2 viruses. HIV-1 regularly shows a strong band, which is attributed to the protein p24, and a very weak band, which is often scarcely visible, which is attributed to the protein p23. HIV-2 exhibits a strong band, which is attributed to the protein p25, and sometimes a weak band, which is to be attributed to the protein p23. In contrast to this, MVP5180/91 virus exhibits two bands of approximately equal strength, which bands correspond to the proteins p24 and p25.

It has been discovered that there is a further significant difference in the bands which are attributed to the reverse transcriptase. HIV-1 shows a band (p53) which corresponds to the reverse transcriptase and a band (p66) which corresponds to the reverse transcriptase combined with the RNAse H. In HIV-2, the reverse transcriptase corresponds to the protein p55 and, when it is combined with the RNAse H, the protein p68. By contrast, MVP5180/91 exhibits a band at protein p48, corresponding to the reverse transcriptase, and a band at protein p60, which corresponds to the reverse transcriptase in combination with RNAse H. Based on these data, the present inventors conclude that MVP5180/91 reverse transcriptase has a molecular weight which is between about 3 and about 7 kilodaltons less than that of the reverse transcriptase of HIV-1 or HIV-2.

A comparison of the nucleic acid and amino acid sequences of HIV-1, HIV-2 and MVP5180/91 reveal other significant differences. Generally, the similarity between different virus isolates is expressed in terms of the degree of "homology," i.e, similarity between the nucleic acid sequences or protein sequences. For example, homology of 50% denotes that 50 out of 100 nucleotide positions or amino acid positions are the same in both sequences. The homology between proteins is determined by sequence analysis. Homologous DNA sequences can also be identified by the hybridization technique according to Southern (Southern E. M., *J. Mol. Biol.* 98: 503–517 (1975)).

The present inventors provide in Table 1 a summary of a sequence comparison between MVP5180/91 and the consensus sequences of HIV-1 and HIV-2, and also the isolate ANT70, a virus designated HIV-3 (WO 89/12094 and EP-A-0 345 375). This comparison demonstrates that in the diagnostically important env gene region, for example, MVP5180/91 possesses sequences which are only 53% homologous to those of HIV-1 and only 49% homologous to those of HIV-2. By contrast, HIV-1 isolates of the subtypes A–E, for example, exhibit, when their genomic nucleotide sequences are compared, a percentage homology among themselves which is appreciably greater. In this case, the values are, without exception, greater than 75%.

| Gene | | Percent Homology (approximate) |
|---|---|---|
| LTR | HIV-1 | 67% |
| | HIV-2 | 51% |
| | ANT 70 | 82% |
| GAG | HIV-1 | 70% |
| | HIV-2 | 62% |
| | ANT 70 | 89% |
| POL | HIV-1 | 74% |
| | HIV-2 | 66% |
| | ANT 70 | 90% |
| VIF | HIV-1 | 68% |
| | HIV-2 | 42% |
| | ANT 70 | 87% |
| ENV | HIV-1 | 53% |
| | HIV-2 | 49% |
| | ANT 70 | 81% |
| NEF | HIV-1 | 54% |
| | HIV-2 | 59% |
| | ANT 70 | 81% |
| total | HIV-1 | 65% |
| | HIV-2 | 56% |

On the basis of these clear differences in sequence, and because MVP5180/91's genomic organization corresponds to that of an HIV-1 virus, the isolate MVP5180/91 was assigned to a new HIV-1 subtype, the subtype O (Myers et al., *Human Retroviruses and AIDS* 1993, "A compilation and analysis of nucleic acid and amino acid sequences," Los Alamos National Laboratory, Los Alamos, USA(1993)). The only other representative of this subtype which is known so far is the above-mentioned isolate ANT70.

Thus, the present invention relates to immunologically active peptides which are distinct from previously known antigens of retroviruses that cause immune deficiency diseases. The term "immunologically active" means that such peptides react with antibodies against HIV viruses which can be present in the blood of patients or blood donors. Customarily, immunologically active peptides contain at least one epitope which gives rise to the formation of antibodies.

The peptides of the present invention are suitable particular, for the diagnostic detection of antibodies against retroviruses that cause immune deficiency. Such retroviruses are of the HIV type. In a preferred embodiment, these peptides are comprised of a consecutive amino acid sequence of at least 15 amino acids, more prefereably of at least 15 to 50, and most preferably of at least 15 to about 35, amino acids selected from the amino acid sequence (SEQ ID NO:1):
VWGIRQLRARLQALETLIQNQQRLNLWGXKGKLIXY TSVKWNTSWSGR,
  where X is C or S. In one embodiment, C represents a cysteine residue in an oxidized state.

"Consecutive amino acid sequences" are understood by the skilled artisan to mean fragments. In the most preferred embodiment, the peptides comprise consecutive amino acids selected from the sequence RLQALETLIQNQQRLNLW GXKGKLIXYTSVKWN (residues 10–42 of SEQ ID NO:1).

The above-described amino acid sequence is represented by the single letter code, where the individual letters have the following meanings: A=alanine, R=arginine, N=asparagine, D=aspartic acid, C=cysteine, Q=glutamine, E=glutamic acid, G=glycine, H=histidine, I=isoleucine, L=leucine, K=lysine, m=methionine, F=phenylalanine, P=proline, S=serine, T=threonine, W=tryptophan, Y=tyrosine and V=valine.

If the above amino acid sequence is depicted in the so-called three-letter code, the following sequence is obtained (SEQ ID NO:1):
Val Trp Gly Ile Arg Gln Leu Arg Ala Arg Leu Gln Ala Leu Glu Thr Leu Ile Gln Asn Gln Gln Arg Leu Asn Leu Trp Gly X Lys Gly Lys Leu Ile X Tyr Thr Ser Val Lys Trp Asn Thr Glu Thr Leu Ile Gln Asn Gln Gln Arg Leu Asn Leu Trp Gly X Lys Gly Lys Leu Ile X Tyr Thr Ser Val Lys Trp Asn Thr Ser Trp Ser Gly Arg,
  where X is Cys or Ser.

In a particularly preferred embodiment, the meanings of X in one peptide are the same, i.e. cysteine is present twice or serine is present twice.

The present inventors have discovered that an epitope of MVP5180/91, which is of principal relevance for diagnosis is located in the region XKGKLIX (residues 29–35 of SEQ ID NO:1). Therefore, it is preferable that the peptide of the present invention contain a region having this amino acid sequence.

In yet another embodiment of the invention, the peptides comprise the epitope of MVP5180/91 and additionally possess, to the right (C-terminal) and/or left (N-terminal) of the epitope, amino acids which are not derived from MVP5180/91, but which are from a corresponding sequence of another virus, a virus, for example, such as those listed in Table 1. A "corresponding sequence" is not identical to those of MVP5180/91 but are "homologous" or similar to such sequence and is from the same region. The degree of homology among various retrovirus regions is set forth above in Table 1. The additional amino acids are particularly important when the peptides are employed in diagnostic tests. If the peptides are bound to a solid phase, as can be the case, for example, in an ELISA test, it is advantageous for the peptide to have an amino acid sequence to the left (N-terminal) of the epitope. If conjugations are being carried out, it is advantageous for the peptide to have a sequence which is homologous with MVP5180/91 to the right (C-terminal) of the main epitope.

In another embodiment, the peptides according to the invention have a length of about 20 to about 30 amino acids.

Within the scope of the present invention, the following peptides are particularly preferred:
MVP601–623 (SEQ ID NO:2): NQQRLNLWGCKGKLI-CYTSVKWN
MVP591–616C (SEQ ID NO:3): RLQALETLIQNQQRLN-LWGCKGKLIC and
(SEQ ID NO:4): RLQALETLIQNQQRLNLWGSKGKLIS In addition to the amino acid sequence which is homologous to MVP5180/91, the peptides according to the invention can, at one or both ends of the peptide, have additional amino acids which are important for particular functions. In this context, these additional amino acids can be amino acids which, for example, facilitate the binding of the peptide to solid phases. If the peptides are prepared recombinantly, the peptides can also contain amino acids which arise as a result of the nature of the recombinant preparation.

The peptides of the present invention also include recombinant peptides, variants of the above described peptides and "mimetics"—compounds having mimotopes which mimic the above describe epitope of MVP5180/91.

Variants include, for example, oligopeptides and polypeptides corresponding to immunologically active portions of the above described peptides and any non-proteinaceous immunologically active portions of a retrovirus or to the above described peptides linked to a carrier.

Variants according to the present invention may be produced by conventional reverse genetic techniques, i.e. by designing a genetic sequence based upon an amino acid sequence or by conventional genetic splicing techniques. For example, variants can be produced by techniques involving site-directed mutagenesis or oligonucleotide-directed mutagenesis. (See, for example, "Mutagenesis of Cloned DNA," in *Current Protocols in Molecular Biology* 8.0.3 et seq., Ausubel, et al. eds. (1989)("Ausubel") but also by means of synthetic methods.

To be used in recombinant expression of a peptide or peptide variant of the present invention, a polynucleotide molecule encoding such a molecule would preferably comprise a nucleotide sequence, corresponding to the desired amino acid sequence, that is optimized for the host of choice in terms of codon usage, initiation of translation and expression of commercially useful amount of the desired peptide or variant. Also, the vector selected for transforming the chosen host organism with such polynucleotide molecule should allow for efficient maintenance and transcription of the sequence encoding the polypeptide. The encoding polynucleotide molecule may code for a chimeric protein; i.e. it can have nucleotide sequence for the peptide molecule operably linked to a non-peptide moiety, such as a signal peptide for the host cell.

Once DNA fragments have been selected, these fragments can be cloned into suitable cloning vectors according to well-known techniques. (Ausubel at 5.0.1 et seq.) The skilled artisan would understand that the peptide-encoding DNA would need to be expressed in such a way so as not to destroy the immunological activity of the product. The artisan would know which host-vector system provides expression in such a way as to avoid proteolysis and denaturation of the peptides. One approach would be to use a vaccinia virus as a vector. This approach would involve preparing a recombinant vaccinia virus-derived vector in which the peptide gene is placed under the control of a promoter, along with translation and secretion signals, suitable for expressing the peptide in a vaccinia-infected host. (U.S. Pat. No. 4,603,112)

The peptides and peptide variants of the present invention may also be prepared using solid-phase synthesis, as described in Merrifield et al. in *The Peptides, Analysis, Synthesis and Biology*, Vol. 2, Academic Press, Ed. Erhard Gross, Johannes Meyerhofer. (See Example 1, below.) Further description of this technique, and of other processes known in the state of the art, can be found in the literature, e.g. M. Bodansky et al., *Peptide Synthesis*, John Wiley & Sons, 2nd Edition (1976).

In addition to the peptides and peptide variants, the present invention encompasses "mimetics," compounds that mimic the above described epitope. One example of a mimetic is an anti-idiotype antibody, that is, an antibody that is produced by immunizing an animal with an antibody which specifically binds the epitope. The anti-idiotype antibody recognizes and conforms to the combining site on the first antibody. Therefore, the shape of its combining site closely resembles the epitope which fit into the combining site of the first antibody. Because an anti-idiotype antibody has a combining site whose shape mimics the original antigen, it can be used in diagnostic assays and in vaccines to generate antibodies which react with the original antigen. (Fineberg & Ertl, *CRC Critical Reviews in Immunology* 7: 269–284 (1987)). Mimetics also include protein or non-protein structures produced through elaborate structural analyses of the above described peptides, as taught in Kahn, M. "Peptide Secondary Structure Mimetics: Recent Advances and Future Challenges" in *Catalytic Asymmetric Cyanohydrin Synthesis*, Georg. Thieme Verlag, Stuttgart, N.Y. (1993).

In another embodiment, the present invention relates to isolated DNA which encodes the above described peptides and to isolated DNA which is complementary to the DNA encoding such peptides.

Such isolated DNA can be employed in hybridization studies to detect the presence of retrovirus nucleic acids and in PCR, such techniques being well-known in the art. Thus, in one embodiment, the present invention relates to a method of detecting in a sample nucleic acids encoding a retrovirus that causes immune deficiency. This method involves hybridizing a labeled DNA molecule to nucleic acids encoding a retrovirus in a sample, wherein the labeled DNA molecule is prepared by labeling the above described DNA molecule with a detectable label, and then detecting the hybridizing by means of the detectable label, according to methods well-known in the art, such as "Immunochemical Protocols in Methods" in *Mol. Biol.,* Hanson, M., Vol. 10, pp. 431–449, Humana Press (1992), hereby incorporated by reference.

In another embodiment, the invention relates to a method of detecting in a sample nucleic acids encoding a retrovirus that causes immune deficiency, involving subjecting the nucleic acids to a Polymer Chain Reaction (PCR), wherein the PCR employs at least two oligonucleotide primers that anneal to a nucleic acid encoding a retrovirus that causes immune deficiency. One of the primers is complementary to a first nucleotide sequence comprising the sequence of the above described DNA molecule, or its complementary sequence. The other primer is complementary to a second nucleotide sequence comprising a nucleic acid molecule encoding a retrovirus that causes immune deficiency. In accordance with this method, a geometrically amplified product is obtained only when the first and second nucleotide sequences occur within the same nucleic acid molecule encoding a retrovirus that causes immune deficiency. The fundamentals of PCR are well-known to the skilled artisan, see, e.g. McPherson, et al., *PCR, A Practical Approach*, IRL Press, Oxford, Eng. (1991), hereby incorporated by reference.

In both of the above methods, by "sample" is meant any body fluid or tissue, including blood, urine, saliva, spinal fluid, semen, peritoneal fluid, and tissue from any part of the body, such as any organ, muscle or skin. A "retrovirus that causes immune deficiency" includes all retroviruses of the HIV group. This includes, but is not limited to MVP5180/91, HIV-1, HIV-2 and HIV-3 and variant strains of these viruses. In accordance with the present invention, the above described DNA can be labeled by any of several techniques known in the art. For instance, such DNA can be labeled by using radioisotopes (Maniatis et al., *Molecular Cloning*, Sect. 11.15–11.16, 2nd Ed., Cold Spring Harbor Lab. Press (1989)) or non-radioactive labels, such as haptens, proteins, digoxigenin, biotin and so forth. Chemically modified DNA can be used so long as the modification does not interfere with hybridization. For instance, acetylaminofluorene (AFF)-is widely used for such purposes ("Immunochemical Protocols in Methods" in *Mol. Biol.,* Manson, M., Vol. 10, pp. 399–408, Humana Press (1992)). Labeling may also be accomplished by modifying DNA using the Klenow fragment of *E. coli* DNA polymerase (Maniatis et al., *Molecular Cloning*, Sect. 11.4, 2nd Ed., Cold Spring Harbor Lab. Press (1989)). Hybridization occurs under hybridizing conditions which are known to the skilled artisan. Detecting hybridization can be accomplished through the use of autoradiography, when the label is a radioisotope or through chemical or enzymatic means, when the label is non-radioactive, according to techniques well-known in the art ("Immunochemical Protocols in Methods" in *Mol. Biol.,* Manson, M., Vol. 10, pp. 431–449, Humana Press (1992)). See Example 1c. It is understood in the art that nucleic acids include both DNA and RNA.

In another embodiment, the present invention relates to method of detecting in a sample an antibody against a retrovirus that causes immune deficiency. This method involves contacting a sample with a diagnostic composition and detecting the presence of antibody bound to the diagnostic composition as a result of the contacting. A "sample" and "a retrovirus that causes immune deficiency" are as described above. A "diagnostic composition" comprises the above described peptide and a detectable label. The label may be directly bound to the peptide or bound to another moiety, such as an antibody, which binds the peptide, depending upon the precise assay. A "detectable label" includes radioisotopes, such as $I^{125}$, and non-radioactive labels, such as enzymes, fluorescein, antibody conjugates and subtrates and other labels known to the skilled artisan. The detection methods according the present invention encompass competitive or sandwich assays, or any assay well-known to the artisan which depends on the formation of an antibody-antigen immune complex. For purposes of this invention, the above described peptide which is a part of the diagnostic composition of the present invention, can be immobilized or labeled. Many carriers are known to the skilled artisan to which the diagnostic agent of the present invention can be bound for immobilization. Well-known carriers include glass, polystyrene, polypropylene, polyethylene, dextran, nylon, amylases, natural and modified celluloses etc. The carrier can be either soluble or insoluble. Immunoassays encompassed by the method of detecting of the present invention include, but are not limited to Enzyme Linked Immunosorbent Assays (ELISA) and those described in U.S. Pat. No. 4,367,110 (double monoclonal antibody sandwich assay); Wide et al., Kirkham and Hunter, eds. *Radioimmunoassay Methods,* E. and S. Livingstone, Edinburgh (1970); U.S. Pat. No. 4,452,901 (western blot); Brown et al.,*J. Biol. Chem.* 255: 4980–4983

(1980) (immunoprecipitation of labeled ligand); and Brooks et al., *Clin. Exp. Immunol.* 39: 477 (1980) (immunocytochemistry), all of which are hereby incorporated by reference.

The peptides and diagnostic compositions of the present invention are suitable for use in a diagnostic kit. Such a kit comprises the peptide of the present invention, and optionally a control—antibody having a known binding affinity for the peptide—and written instructions for using the kit. Typically, such a kit would be comprised of a receptacle being compartmentalized to receive one or more containers such as vials, tubes and the like, such containers holding separate elements of the invention. For example, one container may contain the peptide of the present invention and another container may contain a control. Both positive and negative controls may be included with the kit of the present invention along with a set of written instructions explaining how to use the kit. A kit of this nature can be used in the methods of detecting antibodies against retroviruses, described above.

In another embodiment, the present invention relates to an immunogen comprising an amount of the above described peptide and a physiologically-acceptable excipient therefor, wherein the amount is sufficient to elicit an immune response that is protective of a susceptible mammal against retrovirus infection. Additionally, the present invention relates to a method of immunizing a mammal against retrovirus infection comprising administering the above described immunogen to a mammal in an effective amount.

The term "immunogen" means an antigen which evokes a specific immune response leading to humoral or cell-mediated immunity, in this context, to HIV virus infections, particularly of 0 subtype. "Immunity" thus denotes the ability of the individual to resist or overcome infection more easily when compared to individuals not immunized, or to tolerate infection without being clinically affected. The preferred susceptible mammal is a human. An immune response that is protective prevents or ameliorates a retrovirus infection.

The immunogen of the present invention is further comprised of an acceptable physiological carrier. Such carriers are well-known in the art and include macromolecular carriers. Examples of suitable carriers in mammals include tuberculin PPD, bovine serum albumin, ovalbumin or keyhole limpet hemocyanin. The carrier should preferably be non-toxic and non-allergenic.

The immunogen may be further comprised of an adjuvant such as an aluminum compound, water and vegetable or mineral oil emulsions (e.g., Freund's adjuvant), liposomes, ISCOM (immunostimulating complex), water-soluble glasses, polyanions (e.g., poly A:U, dextran sulphate, lentinan), non-toxic lipopolysaccharide analogues, muramyl dipeptide, and immunomodulating substances (e.g., interleukins 1 and 2) or combinations thereof. The preferred adjuvant is aluminum hydroxide. Immunogenicity can also be enhanced in mammals which have received live attenuated bacterial vectors, such as Salmonella or Mycobacteria, or more importantly, viral vectors like Vaccinia, which express the immunologically active peptide.

Techniques for formulating such immunogens are well-known in the art. For instance, the immunogen may be lypholized for subsequent rehydration in an excipient such as saline or other physiological solution. In any event, the vaccine of the present invention is prepared by mixing an immunologically effective amount of the peptide with the excipient in an amount resulting in the desired concentration of the immunogenically effective component of the vaccine.

The amount of the immunogenically effective component in the vaccine will depend on the mammal to be immunized, with consideration given to the age and weight of the subject as well as the immunogenicity of the immunogenic component in the vaccine. The determination of the precise dosage is a matter within the skill of the art of the invention.

The methods of preparation of the immunogens of the present invention are designed to ensure that the identity and immunological effectiveness of the specific molecules are maintained and that no unwanted microbial contaminants are introduced. The final products are distributed and maintained under aseptic conditions.

The method of immunizing a mammal against HIV infection involves administering to the mammal an effective amount of the foregoing immunogen. Administration may involve any procedure well-known in the art. For instance, a suitable administration strategy may involve administering the above described vaccine to mammals which are most likely to be exposed to HIV virus, prior to the known time of anticipated exposure. Any immunization route which may be contemplated or shown to produce an appropriate immune response can be employed, in accordance with the present invention, although parenteral administration is preferred. Suitable administration forms include subcutaneous, intracutaneous or intramuscular injections or preparations suitable for oral, nasal or rectal administration.

The present invention is described in more detail in the following examples, which are illustrative and in no way intended to limit the scope of the invention.

EXAMPLE 1

Indirect Immunoassay for the HIV Detection of Serotype 0-Specific Antibodies

EXAMPLE 1A

Synthesis of the MVP 601–623 Peptide According to the Invention and Also of the HIV-1 Peptide HIV 601–623

Figure 3:
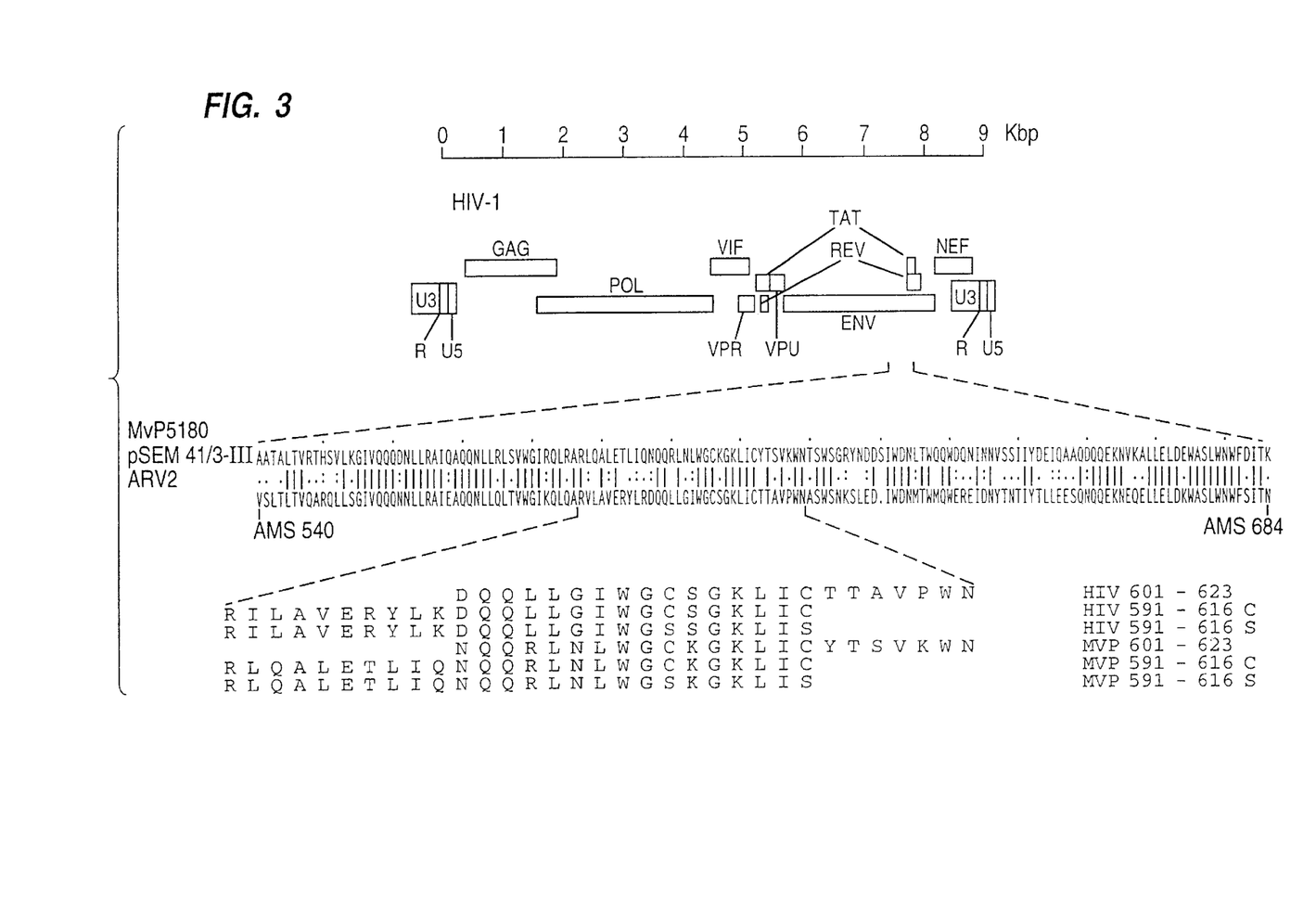
FIG. 3 is a diagram showing the sequence region from MVP5180 gp41, expressed in the recombinant plasmid pSEM 41/3-III, in comparison with the corresponding sequence of the HIV-1 isolate ARV-2. (SEQ ID NOS 2–7, 10 and 11 are shown in this Figure.)

The synthesis of MVP 601–623, NQQRLNLWGCK-GKLICYTSVKWN (SEQ ID NO:2), as shown in FIG. 3, from the transmembrane protein gp41 of MVP5180 was carried out in accordance with Barani, G. and Merrifield, R. B. in *The Peptides, Analysis, Synthesis and Biology,* Vol. 2, Academic Press, Ed. Erhard Gross, Johannes Meyerhofer. The analytical purity was 81% according to HPLC. The reference peptide HIV 60L-623, DQQLLGIWGCS-GKLICTTAVPWN (SEQ ID NO:5) was likewise synthesized by the Merrifield method. The crude peptide was purified by HPLC. The purity is 87%.

FIG. 3 is a diagram showing the sequence region (SEQ ID NO:10) from MVP5180 gp4l, expressed in the recombinant plasmid pSEM 41/3-III, in comparison with the corresponding sequence of the HIV-1 isolate ARV-2 (SEQ ID NO:11). The peptides designated HIV are HIV-1 isolate-derived sequences (SEQ ID NOS:5–7). The peptides designated MVP are MVP5180-derived sequences (SEQ ID NOS:2–4). The numbering of the sequences relates to the data regarding the HIV-1 BH10 env sequence in Rattner et al., *Nature,* 313: 277–284.

EXAMPLE 1B

Preparation of Peptide Solutions and Coating of Microtitration Plates with These Peptides The peptides MVP 601–623 (SEQ ID NO:2) and HIV 601–623 from (SEQ ID NO:5) Example 1a were dissolved in 50% (v/v) acetic acid at a concentration of 6 mg/ml. The stock solutions were diluted in 0.10 M sodium bicarbonate (pH 9.6) such that the concentrations of the polypeptides are 1 µg/ml. 100 µl of the dilute solution were added to each of the wells of type B microtitration plates from Nunc, Roskilde, Denmark. The filled test plates were incubated at 20° C. for 18 hours. The solutions were then sucked off and the wells were rinsed 3–4 times with 300 µl of a 10 g/l solution of bovine serum albumin in phosphate-buffered physiological sodium chloride solution (PBS, pH 7.4), and the test plates were then dried over silica gel at 20° C.

EXAMPLE 1C

Preparation of a Peroxidase-labelled Antibody Against Human Immunoglobulin of the IgG Class (h-IgG), and also TMB Substrate for Detection Monoclonal antibodies against h-IgG were prepared in accordance with the method of Koehler and Milstein, Nature 256: 495, 1975, with different monoclonal antibodies having the same antigen specificity being identified by the method described by Stahli et al., J. of Immunological Methods 32: 297–304 (1980). Following purification by gel chromatography and dialysis against PBS buffer, pH 7.4, the monoclonal antibody fraction (4 mg of protein/ml) was reacted with N-gammamaleimidobutyloxysuccinimide (GMBS) in accordance with Tanamori et al., J. Immunol. Meth. 62: 123–131 (1983). In parallel with this, 2-iminothiolane hydrochloride (from Sigma, Cat. No. 1 6256) was reacted with horseradish peroxidase (POD, from Boehringer Mannheim, Cat. No. 413470) in accordance with King et al. Biochem. 17: 1499–1506 (1978). An antibody/POD conjugate was prepared from the GMBS/antibody conjugate and the iminothiolane/POD conjugate as described by Tanamori et al., supra.

The resulting solution of the IgG/POD conjugate had a protein content of 360 µl/ml. The ratio of POD to IgG was 2.8. The solution was subsequently diluted to 500 ng/ml IgG/POD using a solution of 50 ml/l fetal calf serum (FCS, from Biochrom KG, Berlin) and 5 g/l polyoxyethylene (20) sorbitan monolaurate (Tween 20) in PBS, and was given the designation anti-IgG/POD conjugate. For use in the ELISA, the anti-IgG/POD conjugate was diluted 1:100 to 1:20,000 with Tris buffer (pH 7.4, containing 0.5% Tween 20), and then a series of 1:26 final dilutions in conjugate buffer (0.1 M 1-amino-2-(hydroxymethyi)-1,3-propanediol (Tris), 0.1 M sodium chloride (NaCl) and 0.1% Tween 20, pH 8.4) is prepared.

For detecting anti-human IgG/POD, the present inventors used a substrate system, or a substrate preparation, composed of hydrogen peroxide and tetramethylbenzidine (TMB), which was prepared from two stock solutions as follows:

Stock solution 1: TMB dihydrochloride was dissolved with stirring in double-distilled water at a concentration of 5 g/l (16 mmol/l), and this solution was adjusted to pH 1.5 using 5 N hydrochloric acid. Penicillin G was added to this solution with stirring, up to a final concentration of 200 mg/l (0.56 mmol/l).

Stock solution 2: 1.4 ml of glacial acetic acid, 1.5 ml of 1 N NaOH and 250 mg (3 mmol) of $H_2O_2$, as a urea/hydrogen peroxide adduct, were added to 900 ml of double-distilled water. After these substances had dissolved completely, the solution was made up to 1 liter using double-distilled water.

TMB substrate preparation: One part by volume of stock solution 1 and 10 parts by volume of stock solution 2 were mixed together.

EXAMPLE 1D

Determination of Human Antibodies of the Immunoglobulin G Class Against MVP5180 in an ELISA Using the Peptide According to the Invention 50 µl of serum or plasma were added to 50 vl of sample buffer, containing 0.3 M Tris, 0.3 M NaCl, 20% bovine serum and 0.1% Tween 20, in wells of coated microtiter plates which were prepared in accordance with Example 1b. After the plates had been incubated at 37° C. for 30 minutes, the test solutions were sucked off and the wells were in each case washed five times with washing buffer containing 1 g/l Tween 20 in PBS. After that, 100 µl of conjugate (according to Example 1c) were added to each of the wells, a preliminary dilution of 1:3000 in Tris buffer (pH 7.4, 0.5% Tween 20) and a final dilution of 1:26 in conjugate buffer preferably being selected. After the plates had been incubated at 37° C. for 30 minutes, the contents of the wells were sucked off and the wells were once again in each case washed five times. Subsequently, 100 µl of TMB substrate preparation were added to each well and the plates were incubated at 20–22° C. for 30 minutes; the reaction was then stopped by adding 100 µl of 1 normal sulfuric acid. The extinction of the colored solution was measured at a wavelength of 450 nm (E450) against a blank value of PBS.

In Table 2, the reactivities of Western-blot anti-HIV-1 negative and Western-blot anti-HIV-1 positive samples (all from blood donors from the Cameroons) are compared on microtitration plates which are coated, on the one hand, with the synthetic peptide MVP 601–623 and, on the other, with the synthetic peptide HIV 601–623.

TABLE 2

| Status according to Western blot | Samples, I.D. | Signal/Cut off MVP 601–623 (reagent according to the invention) | Signal/Cut/off HIV 601–623 (Reference) |
|---|---|---|---|
| Anti-HIV negative | 16749 | 0.1 | 0.2 |
|  | 16750 | 0.1 | 0.1 |
| Anti-HIV positive | 17038 | >6 | 0.7 |
|  | 17041 | 0.8 | 3.0 |
|  | 16717 | >6 | >6 |
|  | 16748 | >6 | >6 |
| Cut off |  | 0.400 | 0.400 |

It can be seen from Table 2 that, while some samples (16717 and 16748) clearly react positively in both assays, others (17038) only react with the MVP peptide according to the invention.

EXAMPLE 2

Immunometric Immunoassay for Detecting Serotype O-Specific HIV Antibodies

EXAMPLE 2A

Preparation of the MVP 601–623 Peptide/POD Conjugate 10 mg of the peptide MVP 601–623 (SEQ ID NO:2) according to the invention (Example 1a) were dissolved in 1 ml of glacial acetic acid/water (50:50, v/v). When the solution had been neutralized with 5 N sodium hydroxide solution, a 10-fold molar excess of GMBS was added to it and the mixture was incubated at room temperature for 1 hour. The GMBS which had not reacted was separated off by gel filtration (Sephadex G-25) using 0.1 M sodium phosphate/5 mmol/l nitrilotriacetic acid, pH 6.0. 10 mg of horseradish peroxidase (POD) were incubated, at room temperature for 1 hour, in 5 ml of 10 mmol/l sodium phosphate, 100 mmol/l NaCl, pH 8.0), together with a 100-fold molar excess of 2-iminothiolane. Free modifying reagent was then removed by gel chromatography (Sephadex G-25) using 0.1 M sodium phosphate/5 mmol/l NTA, pH 6.0. The two eluates (SH-activated peroxidase and maleimide-modified HIV-1 peptide) were combined and incubated at room temperature overnight. When the reaction had been stopped using 1/19 vol. of 0.1 M N-ethylmaleimide, the non-reacted HIV-1 peptide was removed from the conjugate by gel chromatography (Sephadex G-25). After the solution has been concentrated (2 mg/ml), the peptide/peroxidase conjugate was stored at −20° C.

EXAMPLE 2B
Immunometric Immunoassay for Detecting Anti-MVP Antibodies

An enzyme immunoassay for detecting anti-HIV antibodies was carried out as follows: 25 µl of sample buffer (0.3 M Tris/HCl, 1% albumin, 2% Tween 20, pH 7.2) were incubated, at 37° C. for 30 minutes, together with 100 µl of human serum in the wells of a test plate coated with HIV peptides. After the wells had been washed 4 times with 50 mmol/l PBS, 0.1% Tween 20, 100 µl of the HIV peptide/peroxidase conjugate prepared in accordance with Example 1b (1:1000 in 0.1 M Tris/HCl, 1% albumin, 2% Pluronic F 64, pH 8.1) were pipetted in.

The 30-minute incubation (+37° C.) is terminated by four further washing steps. The bound peroxidase activity, which correlates directly with the number of bound HIV-1-specific antibody molecules, was determined by adding $H_2O_2$/tetramethylbenzidine (Behringwerke AG, Marburg, FRG)

EXAMPLE 2C
Use of the Diagnostic Composition According to the Invention

Western-blot characterized anti-HIV negative and anti-HIV positive samples (see Example 1 as well) were examined in the immunoassay according to Example 2b. The results (signal/cut off) of this investigation are given in Table 3, as are comparative investigations with a commercial anti-I-HIV assay of the 3rd generation (immunometric test principle).

TABLE 3

| Sample status according to Western blot | Samples, I.D. | Signal/Cut off MVP immunometr. (diag. comp.) according to the invention | Signal/Cut off Anti-HIV (3rd Gen.) Assay, Reference |
|---|---|---|---|
| Anti-HIV negative | 16749 | 0.1 | 0.1 |
| | 16750 | 0.1 | 0.1 |
| Anti-HIV | 17038 | >16.6 | 0.8 |
| | 17041 | 0.6 | 9.5 |
| | 16717 | >16.6 | 14.1 |
| | 16748 | >16.6 | 9.6 |
| Cut-off | | 0.150 | 0.141 |

In this comparison, it is found that, even when the same assay test principle is used, the different antigens are recognized differently, especially in the case of samples 17038 and 17041. The diagnostic composition according to the invention very clearly demonstrates the presence of HIV antibodies in sample 17038, whereas the commercial reference assay reacts inadequately.

EXAMPLE 3
Immunoassay for Selectively Detecting Serotype O-Specific HIV Antibodies

EXAMPLE 3A
Synthesis of the Peptides According to the Invention and of Their Reference Peptides The following 4 peptides were synthesized by the method of Example 1a:
RILAVERYLKDQQLLGIWGCSGKLIC HIV 591–616 C (SEQ ID NO:6) Reference
RILAVERYLKDQQLLGIWGSSGKLIS HIV 591–616 S (SEQ ID NO:7) peptides
RLQALETLIQNQQRLNLWGCKGKLIC MVP 591–616 C (SEQ ID NO:3) Peptides
RLQALETLIQNQQRLNLWGSKGKLIS MVP 591–616 S (SEQ ID NO:4) according to the invention (see FIG. 3)

Following purification of the 4 crude peptides by HPLC, purities of 81%–89% were obtained.

EXAMPLE 3B
Coating and Implementation

The 4 peptides prepared and purified according to Example 3a were dissolved according to Example 1b and coated on microtitration plates. An assay was carried out in accordance with Example 1d.

EXAMPLE 3C
Use of the Diagnostic Composition According to the Invention

The samples from Examples 1 and 2 were tested, in accordance with Example 3b, in an indirect antibody test both for the peptides MVP 591–616 "C" (SEQ ID NO:3) and MVP 591–616 "S" (SEQ ID NO:4) according to the invention and for the reference peptides. The results of these investigations are listed in Table 4.

TABLE 4

| Status according to Western blot | Samples, I.D. | Signal/Cut off MVP 591–616 MVP 591–616 Invention | | Signal/Cut off HIV 591–616 HIV 591–616 Reference | |
|---|---|---|---|---|---|
| | | C | S | C | S |
| Anti-HIV negative | 16749 | 0.6 | 0.6 | 0.5 | 0.5 |
| | 16750 | 0.4 | 0.5 | 0.1 | 0.8 |
| Anti-HIV positive | 17038 | 14.2 | 5.6 | 5.3 | 0.1 |
| | 17041 | 0.3 | 0.3 | 5.1 | 2.8 |
| | 16717 | >16.6 | 0.7 | >8.3 | >8.3 |
| | 16748 | 16.2 | 0.7 | >8.3 | >8.3 |
| cut off | | 0.150 | 0.150 | 0.300 | 0.300 |

As can be seen from Table 4, it is possible to discriminate, in a selective and specific manner, between serotype O-specific and "non"-serotype O-specific HIV antibodies if the signal/cut off values of the MVP 591–616 "S" assay are compared with those of HIV 591–616 "S" assay.

EXAMPLE 4
Immunoassay for the Simultaneour Detection of Serotype A–E and Serotype O-Specific HIV Antibodies

EXAMPLE 4A
Preparation of Peptide Solutions and Coating of Microtitration Plates The peptides MVP 601–623 (SEQ ID NO:2) and HIV 601–623 (SEQ ID NO:5), prepared in accordance with Example 1a, were dissolved in 50% (v/v) acetic acid at a concentration of 6 mg/ml. The stock solutions were mixed in different proportions on a volume basis and diluted in 0.10 M sodium carbonate (pH 9.6) such that the total concentration of the peptides is between 0.125 and 2 µg/ml. As in Example 1b, these solutions were added to microtitration plates and the antigens are coated such plates.

EXAMPLE 4B
Implementation of the Immunoassay and Results

An immunoassay was carried out according to Examples 1c and 1d. The results are summarized in Table 5.

TABLE 5

| Status according to Western blot | Samples, I.D. | Signal/ Cut off MVP 601–623 | Signal/ Cut off HIV 601–623 | Signal/ Cut off MVP 601–623 Invention |
|---|---|---|---|---|
| Anti-HIV negative | 16749 | 0.2 | 0.2 | 0.2 |
|  | 16750 | 0.5 | 0.2 | 0.2 |
| Anti-HIV positive | 17038 | >10 | 0.4 | >10 |
|  | 17041 | 0.5 | 2.5 | 4.7 |
|  | 16717 | >10 | >10 | >10 |
|  | 16748 | >10 | >7 | >10 |
| Cut off |  | 0.250 | 0.250 | 0.250 |

EXAMPLE 5
Immunoassay for Detecting Serotype O-Specific HIV Antibodies Using Recombinant Antigens

EXAMPLE 5A
Construction of the Plasmid pSEM 41/3-III

The present inventors investigated the serodiagnostic importance of the MVP5180/91 gp41 region. To do this, a recombinant expression clone was constructed which contains a constituent region of MVP5180 gp41. The methodology for constructing such plasmids is known (Sambrook, Fritsch, Maniatis, Molecular Cloning, A Laboratory Manual, 2nd Edition, Cold Spring Harbor Laboratory Press, 1989).

A suitable DNA segment from gp41 was obtained by means of PCR (polymerase chain reaction, U.S. Pat. Nos. 4,683,195 and 4,683,202). The following primers were employed for this purpose:

1A: 5' TGTGTGGTACCGCAGCGGCAACAGCGCT-GACG 3' (SEQ ID NO:8) and

1B: 5' GTGTGTCTAGTTTAGTTATGTCAAAC-CAATTC 3' (SEQ ID NO:9)

0.1 µg of plasmid pSP4 DNA was used as template (DE 4318184). The conditions for the PCR were:
1. Initial denaturation: 94° C., 3 min,
2. Amplification: 1.5 min. 94° C., 1 min., 56° C. and 1 min. 72° C. for 30 cycles. Nucleotide and buffer concentrations were used, and Taq polymerase was employed, in accordance with the supplier's (Perkin Elmer) instructions.

The amplified DNA was subsequently digested, at 37° C. for 1 hour, with the restriction endonucleases Asp 718 and XbaI, and the DNA was fractionated in a 1% agarose gel. The DNA band 440 bp in size was cut out of the gel, and the DNA was electroeluted, phenol-extracted, precipitated with ethanol, dried and resuspended in 5 µl of H$_2$O.

0.5 µg of the dissolved, amplified DNA was ligated to 0.5 µg of the Asp718/XbaI-,digested expression vector PSEM 3 (Knapp et al., Biotechniques 8: 280–281 (1990)) (2 Weiss units of lambda T4 ligase, 12 hrs. at 15° C.) and transformed into E. coli XL1 Blue (from Stratagene). The clone resulting from this procedure, harboring the recombinant plasmid pSEM 41/3-III, expresses the MvP5180/gp41-specific peptide as a fusion protein with a fragment of E. coli β-galactosidase.

The expressed MVP5180 sequence is depicted in FIG. 3 (SEQ ID NO:10).

EXAMPLE 5B
Expression and Purification of the MVP 41/3-III Fusion Protein

Escherichia coli XL1 Blue, transformed with the plasmid pSEM 41/3-III (according to Example 5a), was cultivated in Luria broth medium and induced with 1 mM isopropyl thiogalactoside at an optical density of 0.5. After three hours, the cells were centrifuged down, washed with 100 mM sodium phosphate buffer, 10 mM MgCl$_2$, pH 7.5, and, after centrifugation for 10 minutes at 5000×g, resuspended in the same buffer. After adding RNase and DNase, the cell suspension was disrupted using a high-pressure homogenizer at 1000 bar and the homogenate was centrifuged (20 minutes, 80,000×g, 4° C.). The sediment contained the inclusion bodies and was resuspended in 50 mM Tris-HCl, pH 8.0, and 0.5% deoxycholate and centrifuged once again (20 minutes, 100,000×g, 4° C.). The sediment which was obtained was resuspended in 3 M urea, 20 mM Tris-HCl, 0.5 mM phenylmethylsulfonyl fluoride (PMSF) and centrifuged once again (20 minutes, 100,000×g, 4° C.).

The sediment, which already had been washed twice, was subsequently incubated for 1 hour in 5 M guanidine HCl, 10 mM Tris-HCl, 5 mM ethylenediaminetetraacetate (EDTA), 0.5 mM PMSF and 100 mM dithiothreitol. After centrifugation (20 minutes, 100,000×g, 4° C.), the supernatant, which contained the solubilized MVP 41/3-III protein, was purified chromatographically by gel filtration on TSK-HW-55 S (from Merck, Darmstadt) in 5 M guanidine HCl, 10 mM Tris-HCl, 5 mM EDTA, pH 8.0. The product-containing fractions were identified by electrophoresis, combined and transferred, by rebuffering, into 5 M urea, 10 MM Tris-HCl, 5 mM EDTA, pH 8.0.

EXAMPLE 5C
Immunoassay for Detecting Serotype O-specific HIV Antibodies

The recombinant antigen MVP 41/3-III according to the invention, which was purified according to Example 5b, was diluted in 0.1 M sodium carbonate (pH 9.6) such that the concentration of the protein was 0.5 µg/ml.

The antigen was coated on a plate, as described in Example 1b, and the assay which had been set up in this way was carried out as in Example 1d.

EXAMPLE 5D
Results with the Recombinant Antigen in the Immunoassay

The results from the samples which were investigated in accordance with Example 5c are summarized in Table 6:

TABLE 6

| Status according to Western blot | Samples, I.D. | Signal/Cut off MVP 41/3-III (diag. comp. according to the invention) |
|---|---|---|
| Anti-HV negative | 16749 | 0.6 |
|  | 16750 | 0.5 |
| Anti-HIV positive | 17038 | 4.2 |
|  | 17041 | 2.1 |
|  | 16717 | 3.2 |
|  | 16748 | 3.8 |
| cut off |  | 0.500 |

These results clearly show that recombinant proteins from MVP5180/gp41 which contain the region according to the invention are also antigens which are very well suited for detecting both serotype O-specific and "non"-serotype O-specific HIV antisera.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. P 44 05 810.1, filed Feb. 23, 1994, for which benefit under 35 USC §119 is claimed, is expressly incorporated herein in its entirety.

What is claimed is:

1. A method of detecting the presence of nucleic acid of a human immunodeficiency virus in a sample, comprising the steps of:
   (a) providing a sample suspected of containing one or more nucleic acids encoding a protein of an immunodeficiency virus;
   (b) contacting the sample of step a with suitable PCR reagents that comprise at least a first and a second oligonucleotide primer that can anneal to the immunodeficiency virus nucleic acid, wherein the first primer sequence is complementary to a nucleic acid sequence from the region within amino acids 601 to 623 of the transmembrane protein of the MVP5180/91 strain of HIV-1 and the second primer is complementary to a known nucleotide sequence of a protein from HIV-1 or HIV-2; and (c) detecting the presence of a geometrically amplified product after incubation under conditions suitable for amplification using both primers.

2. A method of detecting the presence of nucleic acid of a human immunodeficiency virus in a sample, comprising the steps of:

(a) providing a sample suspected of containing one or more nucleic acids encoding a protein of an immunodeficiency virus;

(b) contacting the sample of step a with a labeled DNA wherein the labeled DNA molecule contains a sequence of the MVP5180/91 strain of HIV-1 corresponding to a region of the transmembrane protein within amino acids 601 to 623 and the label is capable of generating a signal for detection of the labeled DNA under conditions that allow hybridization of the labeled DNA with complementary nucleic acid to form a hybridization solution and (c) detecting a generated signal from the hybridization solution indicating the presence or absence of a nucleic acid encoding the immunodeficiency virus.

* * * * *

```
                              SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 48 amino acids
          (B) TYPE: amino acid
          (C) STRANDEDNESS:
          (D) TOPOLOGY: linear (ix) FEATURE:
          (A) NAME/KEY: Modified-site
          (B) LOCATION: 29
          (D) OTHER INFORMATION: /note= "Xaa represents Cys or Ser"

(ix) FEATURE:
          (A) NAME/KEY: Modified-site
          (B) LOCATION: 35
          (D) OTHER INFORMATION: /note= "Xaa represents Cys or Ser"

(xi) SEQUENCE DESCRIPTION: SEQ ID NO:1:

Val Trp Gly Ile Arg Gln Leu Arg Ala Arg Leu Gln Ala Leu Glu Thr
1               5                   10                  15

Leu Ile Gln Asn Gln Gln Arg Leu Asn Leu Trp Gly Xaa Lys Gly Lys
            20                  25                  30

Leu Ile Xaa Tyr Thr Ser Val Lys Trp Asn Thr Ser Trp Ser Gly Arg
        35                  40                  45

(2) INFORMATION FOR SEQ ID NO:2:

(i) SEQUENCE CHARACTERISTICS:
          (A) LENGTH: 23 amino acids
          (B) TYPE: amino acid
          (C) STRANDEDNESS:
          (D) TOPOLOGY: linear (xi) SEQUENCE DESCRIPTION: SEQ ID NO:2:

Asn Gln Gln Arg Leu Asn Leu Trp Gly Cys Lys Gly Lys Leu Ile Cys
1               5                   10                  15

Tyr Thr Ser Val Lys Trp Asn
            20

(2) INFORMATION FOR SEQ ID NO:3:

(i) SEQUENCE CHARACTERISTICS:
          (A) LENGTH: 26 amino acids
          (B) TYPE: amino acid
          (C) STRANDEDNESS:
          (D) TOPOLOGY: linear (xi) SEQUENCE DESCRIPTION: SEQ ID NO:3:

Arg Leu Gln Ala Leu Glu Thr Leu Ile Gln Asn Gln Gln Arg Leu Asn
1               5                   10                  15
```

```
Leu Trp Gly Cys Lys Gly Lys Leu Ile Cys
            20                  25

(2) INFORMATION FOR SEQ ID NO:4:

(i) SEQUENCE CHARACTERISTICS:
        (A) LENGTH: 26 amino acids
        (B) TYPE: amino acid
        (C) STRANDEDNESS:
        (D) TOPOLOGY: linear (xi) SEQUENCE DESCRIPTION: SEQ ID NO:4:

Arg Leu Gln Ala Leu Glu Thr Leu Ile Gln Asn Gln Gln Arg Leu Asn
1               5                   10                  15

Leu Trp Gly Ser Lys Gly Lys Leu Ile Ser
            20                  25

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:5:

Asp Gln Gln Leu Leu Gly Ile Trp Gly Cys Ser Gly Lys Leu Ile Cys
1               5                   10                  15

Thr Thr Ala Val Pro Trp Asn
            20

(2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS:
        (D) TOPOLOGY: linear (xi) SEQUENCE DESCRIPTION: SEQ ID NO:6:

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys
            20                  25

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS:
        (D) TOPOLOGY: linear (xi) SEQUENCE DESCRIPTION: SEQ ID NO:7:

Arg Ile Leu Ala Val Glu Arg Tyr Leu Lys Asp Gln Gln Leu Leu Gly
1               5                   10                  15

Ile Trp Gly Ser Ser Gly Lys Leu Ile Ser
            20                  25

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear
```

(xi) SEQUENCE DESCRIPTION: SEQ ID NO:8:

TGTGTGGTAC CGCAGCGGCA ACAGCGCTGA CG          32

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear     (xi) SEQUENCE DESCRIPTION: SEQ ID NO:9:

GTGTGTCTAG TTTAGTTATG TCAAACCAAT TC          32

(2) INFORMATION FOR SEQ ID NO:10:

(i) SEQUENCE CHARACTERISTICS:
        (A) LENGTH: 146 amino acids
        (B) TYPE: amino acid
        (C) STRANDEDNESS:
        (D) TOPOLOGY: linear     (xi) SEQUENCE DESCRIPTION: SEQ ID NO:10:

```
Ala Ala Thr Ala Leu Thr Val Arg Thr His Ser Val Leu Lys Gly Ile
1               5                   10                  15

Val Gln Gln Gln Asp Asn Leu Leu Arg Ala Ile Gln Ala Gln Gln His
                20                  25                  30

Leu Leu Arg Leu Ser Val Trp Gly Ile Arg Gln Leu Arg Ala Arg Leu
            35                  40                  45

Gln Ala Leu Glu Thr Leu Ile Gln Asn Gln Gln Arg Leu Asn Leu Trp
        50                  55                  60

Gly Cys Lys Gly Lys Leu Ile Cys Tyr Thr Ser Val Lys Trp Asn Thr
65                  70                  75                  80

Ser Trp Ser Gly Arg Tyr Asn Asp Asp Ser Ile Trp Asp Asn Leu Thr
                85                  90                  95

Trp Gln Gln Trp Asp Gln His Ile Asn Asn Val Ser Ser Ile Ile Tyr
            100                 105                 110

Asp Glu Ile Gln Ala Ala Gln Asp Gln Gln Glu Lys Asn Val Lys Ala
        115                 120                 125

Leu Leu Glu Leu Asp Glu Trp Ala Ser Leu Trp Asn Trp Phe Asp Ile
    130                 135                 140

Thr Lys
145
```

(2) INFORMATION FOR SEQ ID NO:11:

(i) SEQUENCE CHARACTERISTICS:
        (A) LENGTH: 145 amino acids
        (B) TYPE: amino acid
        (C) STRANDEDNESS:
        (D) TOPOLOGY: linear     (xi) SEQUENCE DESCRIPTION: SEQ ID NO:11:

```
Val Ser Leu Thr Leu Thr Val Gln Ala Arg Gln Leu Leu Ser Gly Ile
1               5                   10                  15

Val Gln Gln Gln Asn Asn Leu Leu Arg Ala Ile Glu Ala Gln Gln His
                20                  25                  30

Leu Leu Gln Leu Thr Val Trp Gly Ile Lys Gln Leu Gln Ala Arg Val
            35                  40                  45
```

-continued

```
Leu Ala Val Glu Arg Tyr Leu Arg Asp Gln Gln Leu Leu Gly Ile Trp
     50                  55                  60

Gly Cys Ser Gly Lys Leu Ile Cys Thr Thr Ala Val Pro Trp Asn Ala
 65              70                  75                      80

Ser Trp Ser Asn Lys Ser Leu Glu Asp Ile Trp Asp Asn Met Thr Trp
             85                  90                  95

Met Gln Trp Glu Arg Glu Ile Asp Asn Tyr Thr Asn Thr Ile Tyr Thr
            100                 105                 110

Leu Leu Glu Glu Ser Gln Asn Gln Gln Glu Lys Asn Glu Gln Glu Leu
            115                 120                 125

Leu Glu Leu Asp Lys Trp Ala Ser Leu Trp Asn Trp Phe Ser Ile Thr
            130                 135                 140

Asn
145
```